(12) United States Patent
Erwin et al.

(10) Patent No.: US 11,518,685 B2
(45) Date of Patent: Dec. 6, 2022

(54) CONVERSION OF AMMONIUM NITRATE INTO USEFUL PRODUCTS

(71) Applicant: Southwest Research Institute, San Antonio, TX (US)

(72) Inventors: Jimell Erwin, San Antonio, TX (US); Michael P. Hartmann, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 129 days.

(21) Appl. No.: 17/248,622

(22) Filed: Feb. 1, 2021

(65) Prior Publication Data

US 2021/0238047 A1    Aug. 5, 2021

Related U.S. Application Data

(60) Provisional application No. 62/968,608, filed on Jan. 31, 2020.

(51) Int. Cl.
| | |
|---|---|
| *C01C 1/02* | (2006.01) |
| *C01B 21/02* | (2006.01) |
| *C01B 3/44* | (2006.01) |
| *B01J 21/12* | (2006.01) |
| *B01J 31/16* | (2006.01) |
| *C07C 67/40* | (2006.01) |

(52) U.S. Cl.
CPC ............ *C01C 1/026* (2013.01); *B01J 21/12* (2013.01); *B01J 31/1691* (2013.01); *C01B 3/44* (2013.01); *C01B 21/02* (2013.01); *C07C 67/40* (2013.01); *B01J 2231/49* (2013.01); *B01J 2531/842* (2013.01); *C01B 2203/0227* (2013.01); *C01B 2203/1047* (2013.01); *C01B 2203/1241* (2013.01)

(58) Field of Classification Search
CPC ... C01B 3/44; C01B 21/02; C01B 2203/0227; C01B 2203/1047; C01B 2203/1241; B01J 21/12; C07C 67/40; C07C 67/39; C01C 1/026
See application file for complete search history.

(56) References Cited

U.S. PATENT DOCUMENTS

2008/0245450 A1    10/2008    Villamagna et al.

FOREIGN PATENT DOCUMENTS

KR    20170060834    6/2017

OTHER PUBLICATIONS

Shalini Chaturvedi et al., Review on Thermal Decomposition of Ammonium Nitrate, Journal of Energetic Materials, 31: pp. 1-26, 2019.
Melvin A Cook et al., Explosive Sensitivity of Ammonium Nitrate-Hydrocarbon Mixtures, Industrial and Engineering Chemistry, vol. 43, No. 5, May 1951, pp. 1098-1102.
Stephen H. Crolius, Methane to Ammonia via Pyrolysis, Ammonia Energy Association, Jan. 27, 2017, 7 pages.
(Continued)

*Primary Examiner* — Jafar F Parsa
(74) *Attorney, Agent, or Firm* — Grossman, Tucker, Perreault & Pfleger, PLLC

(57) ABSTRACT

The present invention is directed at the conversion of ammonium nitrate and related compounds upon reaction with methane into compounds such as ethyl acetate, ammonia, nitrogen and hydrogen. The reaction may proceed within a fluid-solid type reactor. The reaction may be facilitated in the presence of inert or catalytic solids.

12 Claims, 2 Drawing Sheets

(56) References Cited

OTHER PUBLICATIONS

Righard Gunawan, Thermal stability and kinetics of decomposition of ammonium nitrate in the presence of pyrite, Journal of Hazardous Materials 165, Nov. 1, 2008, pp. 751-758.
Koji Inazu, Decomposition of ammonium nitrate in aqueous solution using supported platinum catalysts, Catalysis Today 93-95, Jul. 19, 2004, pp. 263-271.
Joseph H. Macneil et al., Catalytic Decomposition of Ammonium Nitrate in Superheated Aqueous Solutions, J. Am. Chem. Soc, 119, May 19, 1997, pp. 9738-9744.
Valery P. Sinditskii, et al. Ammonium Nitrate: Combustion Mechanism and the Role of Additives, Propellants, Explosives, Pyrotechnics 30, 2005, No. 4, pp. 269-280.
International Search Report and Written Opinion dated Apr. 15, 2021, issued in PCT International Patent Application No. PCT/US2021/070103, 7 pages.

CONVERSION OF AMMONIUM NITRATE INTO USEFUL PRODUCTS

CROSS-REFERENCE TO RELATED APPLICATIONS

This application claims the benefit of U.S. Provisional Application Ser. No. 62/968,608 filed Jan. 31, 2020, which is fully incorporated herein by reference.

FIELD

The present invention is directed at the conversion of ammonium nitrate and related compounds upon reaction with methane into compounds such as ethyl acetate, ammonia, nitrogen and hydrogen. The reaction may proceed within a fluid-solid type reactor.

BACKGROUND

Ammonium nitrate ($NH_4NO_3$) has a number of commercial applications, such as use in agriculture as a fertilizer and it is also utilized as a component of explosive mixtures. For example, it is a major component of ammonium nitrate/fuel oil (ANFO), an industrial explosive that reportedly accounts for 80% of explosives utilized in North America. It therefore remains useful to develop reaction schemes that may therefore utilize and convert ammonium nitrate and related compounds to other commercially useful chemical compounds for distribution in the marketplace.

SUMMARY

A method of converting ammonium nitrate and related compounds into secondary products comprising providing ammonium nitrate and reacting with methane in the presence of water in a fluid-solid reactor and forming ethyl acetate, ammonia, nitrogen and hydrogen.

A method of converting nitramine solution into secondary products comprising providing nitramine solution and reacting with methane in the presence of water in a fluid-solid reactor and forming ethyl acetate, nitrogen, and hydrogen.

DETAILED DESCRIPTION

Figure 1:
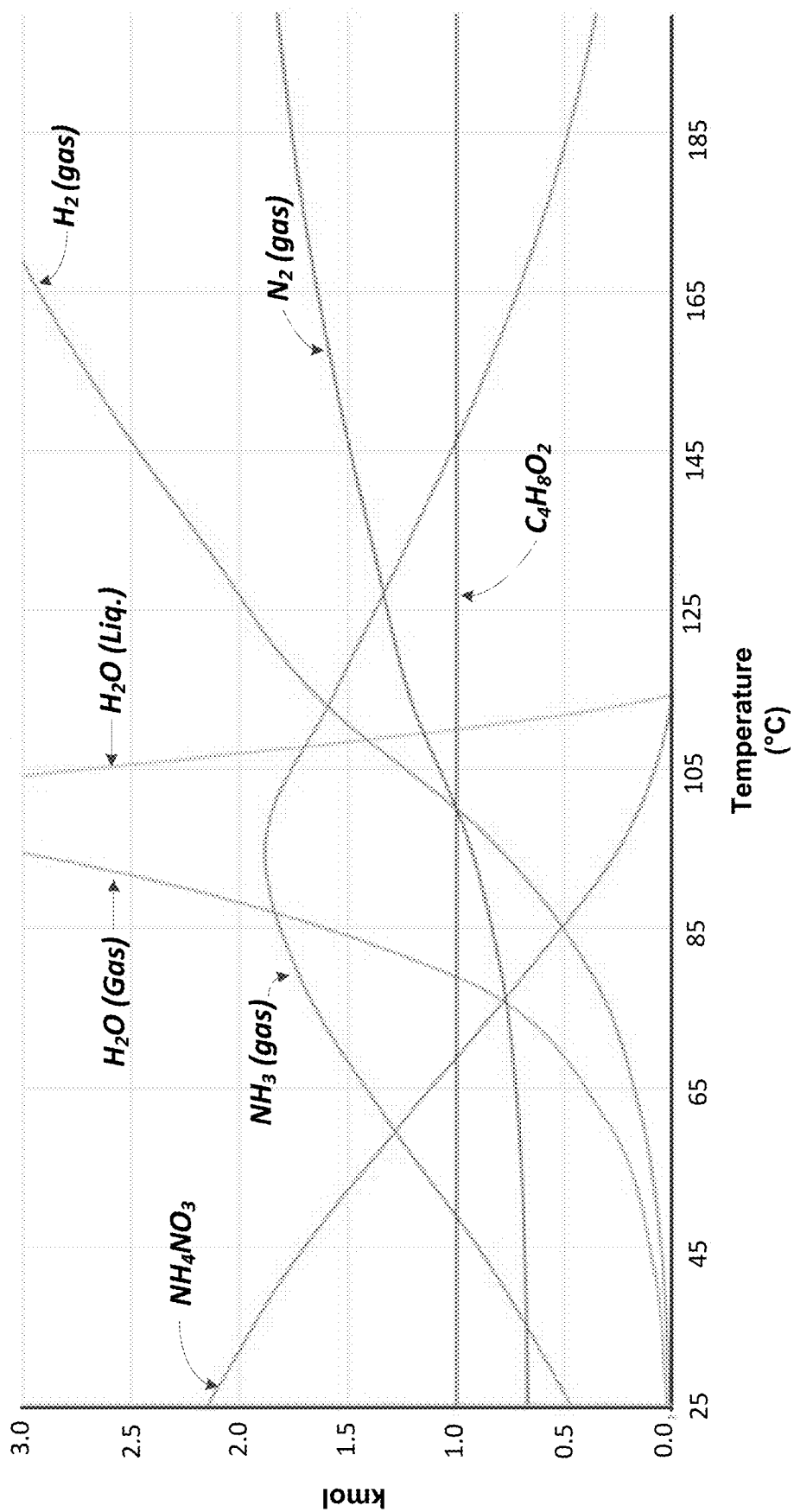
FIG. 1 provides a plot of the temperature dependent results of modeling according to the Gibbs enthalpy minimization reactor model for the reaction of ammonium nitrate with methane.

The present invention provides a method for converting ammonium nitrate ($NH_4NO_3$) solution and related compounds to other products, such as commercially useful chemicals that may be provided to the marketplace. Preferably, the method involves combining ammonium nitrate ($NH_4NO_3$) and related compounds such as nitramines with methane to form such otherwise useful compounds. The methane may preferably be sourced from natural gas. The as-formed useful compounds can include ethyl acetate ($C_4H_8O_2$), ammonia, nitrogen, and hydrogen. The reaction can also preferably be carried out on the solids of a fluid-solid reactor, such as a fluidized-bed reactor. The balanced reaction can be summarized as follows:

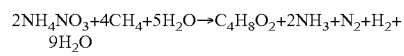

Preferably, the above reaction is configured such that the ammonium nitrate and methane are exposed to elevated temperatures and pressure, where as shown, the reaction leads primarily to the formation of ammonia, ethyl acetate and hydrogen. It can be noted that these are the products that one projects from a Gibbs enthalpy minimization reactor model at temperatures above about 115° C., for which the reaction equilibrium is calculated by minimizing the Gibbs free energy (at specified temperature and pressure) or maximizing entropy.

The related compounds herein are contemplated to include nitramines. Such nitramines may be understood as a family of compounds having the formula $RNHNO_2$ where R may comprise various organic substituents (e.g., alkyl, aromatic, or alkyl-aromatic). Accordingly, by way of example, one may employ methylenedinitramine ($O_2NNHCH_2NHNO_2$) or N-nitroacetamide ($H_3C-CO-NHNO_2$). For example, when R=$-C_2H_3O$:

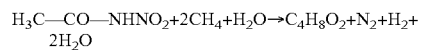

In addition, in the above equation, it is contemplated that one may utilize other nitramines where R in $RNHNO_2$ can have different ratios of C:H:O that are different from the example of 2:3:1. In addition, the conversion of nitramines can optionally produce ammonia.

As alluded to above, the subject reaction is also preferably conducted in a fluid-solid reactor, where a fluid (gas or liquid) is passed through a vessel containing solid granular material at relatively high velocity to suspend the solid and cause it to behave as a fluid. Via use of a fluid-solid reactor, such as a fluidized bed reactor, it may be appreciated that any solid impurities within the reaction may then be preferentially trapped on the circulating solid and may then be disposed of via control of an emerging slip-stream (stream of solid employed in the particular fluidized bed reactor that may be utilized). In addition, it can therefore be appreciated that with reference to the above equation, one can then readily separate and recover any produced water vapor, hydrogen, ammonia, and/or nitrogen as well as any unreacted methane. Any such recovered unreacted methane may then be reused in the system.

Preferably, a catalyst may be employed as the circulating solid in the fluidized bed reactor. Such catalyst may preferably include iron catalyst as in an iron carbide or a metal organic framework (i.e. compounds comprising metal ions or clusters coordinated to organic ligands). The iron carbide used for the circulating catalyst, nominally Fe3C, may be cementite or a similar substance with a ratio of iron to carbon in the approximate ratio or 3:1. The MOF catalyst may be the product of solvothermal synthesis or similar production methods resulting iron-carbon bonds in a framework of suitable linker molecules in the higher valence state of iron. Iron-containing MOFs such as MIL-53(Fe), MIL-100(Fe), or Basolite F300, may be used to derive iron-carbide catalysts.

However, the circulating solids in the fluidized bed reactor need not provide catalysis, as it is contemplated that the solid surfaces alone will provide the necessary pyrolysis of an ammonium nitrate solution with methane as described herein.

FIG. 1 provides a plot of the temperature-dependent results of modeling according to the Gibbs enthalpy minimization reactor model for the reaction herein of ammonium nitrate with methane. As can be observed, ethyl acetate ($C_8H_4O_2$) forms readily from the reaction with methane and no ammonium nitrate remains in the temperature range of the plot from a stoichiometric feed stream. The ammonia ($NH_3$) that forms shares an undesirable equilibrium with nitrogen and hydrogen yielding the latter two gases as the temperature increases. The liquid ammonia produced could be sold or burned for a non-$CO_2$ source of energy. As can therefore be observed, the ammonium nitrate can be converted upon reaction with methane yielding other useful secondary products such as hydrogen, nitrogen, and ammonia.

Figure 2:
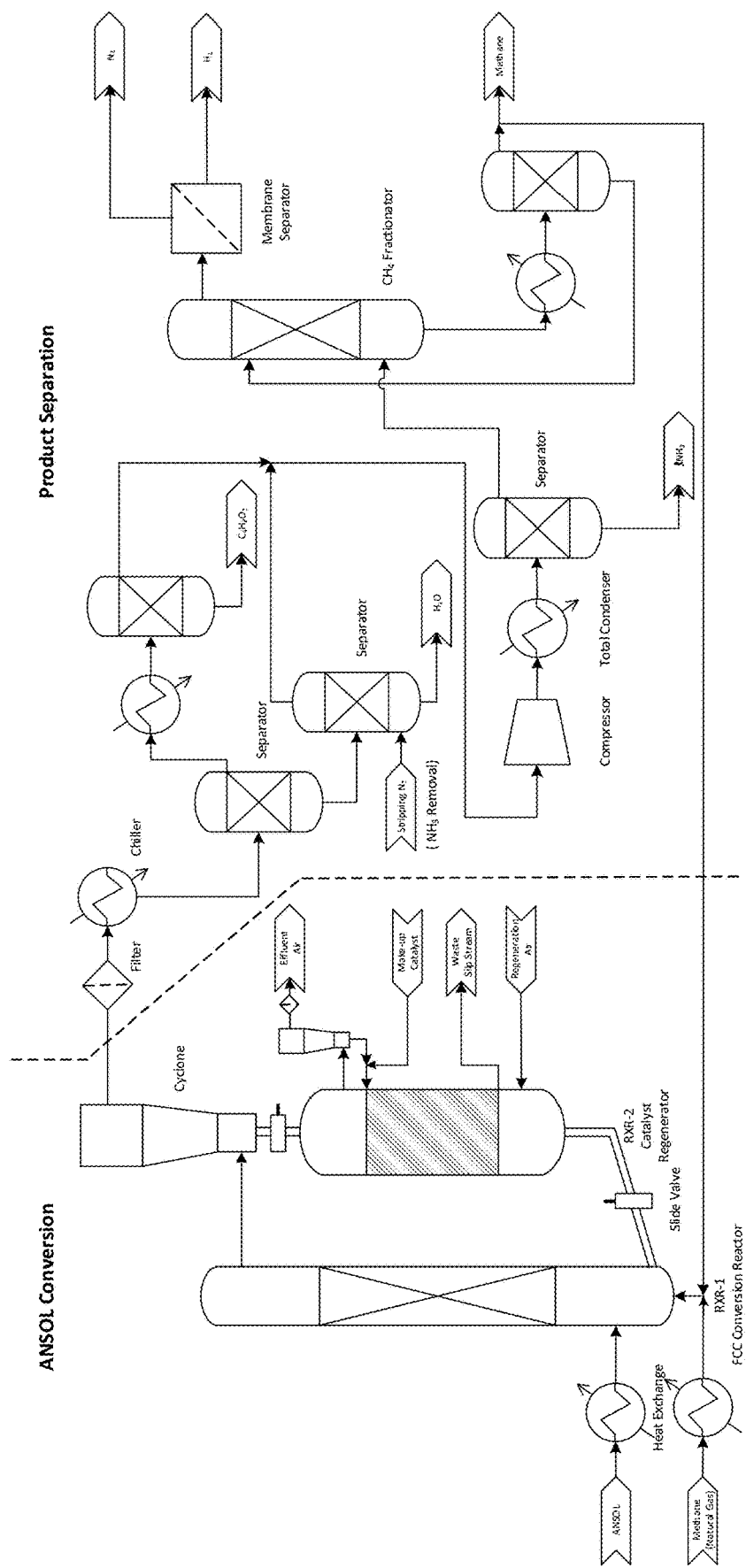
FIG. 2 is a contemplated operations diagram identifying a plant procedure for conversion of ammonium nitrate therein to the identified products.

FIG. 2 is a contemplated operations diagram identifying a plant procedure for conversion of ammonium nitrate herein to the identified products. As can be observed, the ammonium nitrate solution and methane feed as provided from natural gas are sent to a fluidized bed, catalytic cracking (FCC), or other chemical reactor for the primary conversion into ethyl acetate and other gaseous products. As the ammonium nitrate and other nitrogen-bearing compounds decompose, they react with the heated methane in the presence of water to form the favorable thermodynamic distribution of products illustrated FIG. 1. As also can be observed from FIG. 2, the conversion can preferably be made continuous, in the sense that any recovered methane may be recycled for further subsequent reaction with the ammonium nitrate in the conversion reactor.

It is contemplated that the complete destruction of the ammonium nitrate solution will be assured by the residence time provided in the FCC reactor. Preferably, a uniform temperature within the FCC reactor will prevent attaining other relatively high temperatures (i.e. above 600° C.) that would otherwise lead to the decomposition of the ethyl acetate and ammonia into CO, $CO_2$, $H_2$, and $N_2$. Accordingly, it is preferred herein to run the reaction of ammonium nitrate with methane in the fluidized bed reactor at temperatures of ≤600° C., more preferably 300° C. to 600° C. The presence of abundant water is also contemplated to be an inhibiting factor against the autothermic reaction of the energetic nitrogen compounds making the system relatively safe from uncontrolled decomposition reactions. The addition rate of the ammonium nitrate solution and gas circulation rate can be independently varied to optimize the reaction, for example, at a reaction time of 0.25 seconds to 5.0 seconds.

It is also contemplated that different solids may be used in the fluidized bed to improve the reaction of ammonium nitrate as disclosed herein. For example, it is contemplated that an improved reaction rate will be achieved via use of a fluidized bed containing iron catalyst. Alternatively, it is contemplated that the fluidized bed may rely upon aluminosilicate particles to reduce cost, and the porosity of the solid particles in the fluidized bed may be conveniently varied to retain insolubles or other heteroatoms such as metals, e.g., any accumulated waste in the ammonium nitrate starting material.

It is contemplated that the approach herein will offer advantages over the hydrogen reduction of ammonium nitrate solution to ammonia from the perspective that it would not require the use of expensive hydrogen gas and that it provides the various marketable products identified in FIGS. 1 and 2. In addition, any undesirable impurities contained in the ammonium nitrate solution will be accumulated on the circulating solids in the fluidized bed that is relied upon in the process. The reaction and plant procedure identified herein is also one that is contemplated to be: (1) scaleable, with operation over a relatively wide range of throughputs using the same equipment; (2) safe, in the sense that the wet reacting system is one that is contemplated to suppress unwanted uncontrolled decomposition of the reacting components; (3) efficient, in the sense that the methane and nitrogen that are produced are expected to be available for recycling; (4) only relatively small amounts of $CO_2$ would be produced from any fluidized bed solids regeneration and in a form that could be captured, if desired; and (5) the relative temperature uniformity of the conversion of ammonium nitrate upon reaction with methane in a fluidized bed would reduce or avoid conversion to otherwise unwanted products.

Accordingly, the present disclosure identifies a process using chemical reduction by methane to convert ammonium nitrate solution into ethyl acetate and other salable products. The process is amenable to relatively wide and varying size-range using a fluidized bed reactor to convert the ammonium nitrate and other constituents preferably leaving any contaminants on a purge stream of solids. In the identified water-rich environment, the energetic reactions are preferably suppressed for process safety.

The invention claimed is:

1. A method of converting ammonium nitrate solution into secondary products comprising: providing ammonium nitrate solution and reacting with methane in the presence of water in a fluid-solid reactor and forming ethyl acetate, ammonia, nitrogen, and hydrogen.

2. The method of claim 1 wherein methane is provided by a feed of natural gas.

3. The method of claim 1 wherein the reaction is run at a temperature of less than or equal to 600° C.

4. The method of claim 1 wherein unreacted methane is recovered from said reaction of ammonium nitrate with methane and recycled for use for additional reaction of ammonium nitrate with methane in a continuous process.

5. The method of claim 1 wherein said fluid-solid reactor contains solid particles comprising aluminosilicates.

6. The method of claim 1 wherein said fluidized bed reactor includes solid particulate providing a catalyst and carrying out catalytic conversion of said ammonium nitrate to ethyl acetate, ammonia, nitrogen, and hydrogen.

7. The method of claim 6 wherein said catalyst comprises solid particles containing iron.

8. The method of claim 1 wherein said fluidized bed reactor includes solid particulate which absorbs impurities and which solid particulate with said impurities is removed from said fluidized bed.

9. The method of claim 1 wherein said fluid-solid reactor contains solid particles comprising metal organic framework particles.

10. The method of claim 1 wherein said converting of ammonium nitrate solution into secondary products proceeds according to the following reaction:

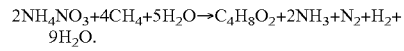

11. A method of converting nitramine solution into secondary products comprising:
provide nitramine solution and reacting with methane in the presence of water in a fluid-solid reactor and forming ethyl acetate, nitrogen, and hydrogen.

12. The method of claim 11 wherein said converting of said nitramine solution into secondary products proceeds according to the following reaction:

* * * * *